United States Patent
Klauber et al.

(10) Patent No.: US 9,701,604 B2
(45) Date of Patent: Jul. 11, 2017

(54) PROCESS FOR PURIFYING 2,5-DICHLOROPHENOL

(71) Applicant: BASF SE, Ludwigshafen (DE)

(72) Inventors: Eric George Klauber, Bad Duerkheim (DE); Michael Rack, Eppelheim (DE); Thomas Zierke, Boehl-Iggelheim (DE); Sebastian Wloch, Ludwigshafen (DE); Nicole Holub, Mannheim (DE); Stefan Dudenhoeffer, Ludwigshafen (DE); Gerald Schmelebeck, Buna, TX (US); Junmin Ji, Beaumont, TX (US); David Cortes, Quincy, IL (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/101,080

(22) PCT Filed: Dec. 1, 2014

(86) PCT No.: PCT/EP2014/076140
§ 371 (c)(1),
(2) Date: Jun. 2, 2016

(87) PCT Pub. No.: WO2015/082415
PCT Pub. Date: Jun. 11, 2015

(65) Prior Publication Data
US 2016/0304425 A1    Oct. 20, 2016

(30) Foreign Application Priority Data
Dec. 23, 2013 (EP) ..................................... 13199434

(51) Int. Cl.
*C07C 37/70* (2006.01)
*C07C 37/84* (2006.01)
*C07C 37/74* (2006.01)

(52) U.S. Cl.
CPC .............. *C07C 37/74* (2013.01); *C07C 37/84* (2013.01)

(58) Field of Classification Search
CPC ................................ C07C 37/74; C07C 37/84
USPC .......................................................... 568/750
See application file for complete search history.

(56) References Cited

U.S. PATENT DOCUMENTS

| 3,013,054 A | 12/1961 | Richter |
| 3,726,929 A | 4/1973 | Payne et al. |

FOREIGN PATENT DOCUMENTS

DE          3512877         11/1986

OTHER PUBLICATIONS

Noelting et al., "Zur Kenntniss des Amido-p-dichlorbenzols," Berichte der Deutschen Chemischen Gesellschaft, (1905), p. 3506.
International Search Report, issued in PCT/EP2014/076140, dated Feb. 3, 2015.
International Preliminary Report on Patentability, issued in PCT/EP2014/076140, dated Jun. 7, 2016.

*Primary Examiner* — Sikarl Witherspoon
(74) *Attorney, Agent, or Firm* — Brinks Gilson & Lione

(57) ABSTRACT

A process for purifying 2,5-dichlorophenol, the process comprising the steps of distillation and subsequent crystallization.

13 Claims, No Drawings

PROCESS FOR PURIFYING 2,5-DICHLOROPHENOL

This application is a National Stage application of International Application No. PCT/EP2014/076140, filed Dec. 1, 2014, which claims the benefit of U.S. Provisional Application No. 61/911,509, filed Dec. 4, 2013. This application also claims priority under 35 U.S.C. §119 to European Patent Application No. 13199434.5, filed Dec. 23, 2013.

The present invention relates to a process for purifying 2,5-dichlorophenol. In a preferred embodiment, the present invention provides a process for purifying 2,5-dichlorophenol with improved purity and/or improved overall yield. 2,5-Dichlorophenol is an important intermediate in the production of the herbicide dicamba (3,6-dichloro-2-methoxybenzoic acid).

BACKGROUND OF THE INVENTION

Dicamba is a selective herbicide currently used for treating e.g. corn, wheat or grassland. It kills broadleaf weeds before and after they sprout. The trivial name dicamba refers to the compound 3,6-dichloro-2-methoxybenzoic acid.

Dicamba is typically produced on an industrial scale from 2,5-dichlorophenol using carboxyla-tion under Kolbe-Schmitt conditions, methylation and subsequently saponification/acidification. 2,5-Dichorophenol in turn can be obtained from 1,4-dichlorobenzene or 1,2,4-trichlorobenzene. The synthetic route via 1,4-dichlorobenzene involves nitration and subsequent diazotation, and, therefore is undesired for use on an industrial scale. The synthetic route via 1,2,4-trichlorobenzene suffers from limited availability of this starting material and from the formation of several byproducts which are formed in the synthesis of 2,5-dichlorophenol.

In order to meet the increasing market demand for compounds such as dicamba, there is a need in the art for processes providing 2,5-dichlorophenol with acceptable purity and/or better overall purification efficiency, so that the limited resources of this compound can be used more efficiently.

The object of the present invention is to meet the above need. In particular, it is the object of the present invention to provide a process for purifying 2,5-dichlorophenol with improved overall purification efficiency and/or high purity. The process according to the present invention is cost effective and can be carried out on an industrial scale.

SUMMARY OF THE INVENTION

The present invention relates to a process for purifying 2,5-dichlorophenol, the process comprising the steps of:
(i) subjecting a mixture (M) comprising 2,5-dichlorophenol, 2,4-dichlorophenol and optionally 3,4-dichlorophenol to distillation to obtain a distillate (D), and
(ii) subjecting the distillate (D) to a crystallization step to obtain a crystalline fraction (C) and a mother liquor (L).
In a preferred embodiment, the above process further comprises the step of:
(iii) combining a composition obtained from the mother liquor (L) in step (ii) with a feed (F), comprising 2,5-dichlorophenol, 2,4-dichlorophenol and optionally 3,4-dichlorophenol, to obtain mixture (M) to be subjected to distillation in step (i).

Processes for purifying mixtures comprising 2,5-dichlorophenol are known in the art. For example, DE 35 12 877 describes a process for obtaining 2,5-dichlorophenol from an isomeric mixture with 2,4-dichlorophenol using recrystallization from water. In single crystallization processes, the large amounts of the 2,5-dichlorophenol remain in the mother liquor so that the overall purification efficiency is low. On the other hand, if crystallization is carried out to an extent so as to recover a higher fraction of 2,5-dichlorophenol, the resulting degree of purity suffers. Furthermore, processes involving more than one crystallization step, in order to increase the amount of 2,5-dichlorophenol separated from the mother liquor, require high efforts and cost.

The present inventors have found that a hybrid purification process involving distillation and crystallization can be employed for purifying 2,5-dichlorophenol with a high degree of purity and an increased overall purification efficiency.

The present inventors also investigated distillation as an alternative method for separating 2,5-dichlorophenol from typical impurities such as 2,4-dichlorophenol and/or 3,4-dichlorophenol. However, the present inventors found that the vapor pressures of especially 2,5-dichlorophenol and 2,4-dichlorophenol are too similar to allow for efficient separation in distillation columns of reasonable size. On the other hand, it has been found that a step of distilling a mixture comprising 2,5-dichlorophenol, 2,4-dichlorphenol and optionally 3,4-dichlorophenol can provide a composition enriched in 2,5-dichlorophenol content sufficient for effective crystallization. Thus, according to the present invention, a feed comprising 2,5-dichlorophenol, 2,4-dichlorphenol and optionally 3,4-dichlorophenol is subjected to a distillation step (i) and the obtained distillate (D) is subjected to a crystallization step (ii) to obtain a crystalline fraction (C) of purified 2,5-dichlorophenol and a mother liquor (L).

In a preferred embodiment according to the present invention, a composition obtained from the mother liquor (L) is combined with a feed (F), comprising 2,5-dichlorophenol, 2,4-dichlorphenol and optionally 3,4-dichlorophenol, to obtain a mixture (M) that can be recycled into the distillation step (i). Depending on how the crystallization step (ii) is carried out as described in further detail below, the composition obtained from the mother liquor (L) can be provided after separation from a solvent or the mother liquor (L) can be used directly, in case no solvent is used during crystallization. Thus, mixing ratio of the composition obtained from the mother liquor (L) and of the (fresh) feed (F) can be adjusted such that a high overall purification efficiency is obtained in the distillation step (i) and a high degree of purity is obtained in the crystallization step (ii).

In a preferred embodiment, the feed (F) is obtained from hydrolyzing 1,2,4-trichlorophenol in the presence of an alkali metal hydroxide or alkali metal alkoxide as described in further detail below. The product mixture obtained in this reaction typically includes major amounts of 2,5-dichlorophenol and impurities such as 2,4-dichlorophenol and/or 3,4-dichlorophenol. Thus, in a preferred embodiment, the above mixture (M) and/or the feed (F) comprises 40 to 95 wt.-%, more preferably 50 to 85 wt.-%, particular preferably 40 to 80 wt.-% of 2,5-dichlorophenol; 5 to 60 wt.-%, more preferably 10 to 40 wt.-%, particular preferably 10 to 20 wt.-% of 2,4-dichlorophenol and optionally 0 to 30 wt.-%, more preferably 5 to 25 wt.-%, particular preferably 10 to 20 wt.-% of 3,4-dichlorophenol.

As mentioned above, the present inventors have found that a distillation step is suitable to fulfill the feed requirements of the crystallization step, i.e., to provide a suitable fraction of 2,5-dichlorophenol in the distillate for feeding to the crystallizer. Furthermore, a distillation step is suitable to significantly reduce the amount of other major impurities such as especially 3,4-dichlorophenol, and to keep the overall yield high. Thus, in a preferred embodiment, the distillate (D) obtained in step (i) comprises 50 to 95 wt.-%, more preferably 55 to 85 wt.-%, particular preferably 60 to 80 wt.-% of 2,5-dichlorophenol.

The distillation step (I) is typically carried out in a distillation column known in the art. In a preferred embodiment, the distillation step (i) is carried out a pressure of 5 kPa to 25 kPa, more preferably 5 kPa to 20 kPa, particular preferably 8 kPa to 20 kPa, and a bottom temperature of 60° C. to 230° C., more preferably 65° C. to 215° C., particular preferably 70° C. to 200° C. The temperature at the column head depends on the boiling point of the mixture under the given pressure and will typically be around 60° C.

Thus, a distillate (D) can be obtained comprising 2,5-dichloropenol in amounts sufficiently high for effective crystallization for obtaining an acceptable degree of purity. Accordingly, in a preferred embodiment of the invention, the crystalline fraction (C) obtained in step (ii) comprises 80 to 99.9 wt.-%, more preferably 85 to 99.9 wt.-%, particular preferably 90 to 99.9 wt.-% of 2,5-dichlorophenol.

There are various options in the art as how to carry out the crystallization step. For example, the mixture obtained after distillation may be crystallized from a supersaturated solution in a suitable solvent, such as recrystallization from water as described in DE 35 12 877. However, it will be necessary to remove the solvent from the obtained mother liquor (L) after crystallization. In a preferred embodiment, the crystallization step (ii) is carried out from a melt. The temperature during melt crystallization typically is high enough to initially provide a melt but low enough to allow for crystallization of 2,5-dichlorophenol. Thus, the temperature during melt crystallization is typically between 15° C. and 55° C. There are also various options as how to carry out crystallization from a melt. For example, layer melt crystallization like static or dynamic layer melt crystallization or suspension melt crystallization may be used. According to one embodiment of the invention, suspension melt crystallization is preferred.

DETAILED DESCRIPTION OF THE INVENTION

In the following, illustrative embodiments of the present invention are described in more detail.

The present invention provides an improved process for purifying 2,5-dichlorophenol. As out-lined above, 2,5-dichlorophenol is an important intermediate for the chemical synthesis of the herbicide dicamba. 2,5-Dichlorophenol can be obtained by hydrolyzing 1,2,4-trichlorobenzene. Conventional processes for hydrolyzing 1,2,4-trihalobenzene are typically carried out using an alkali metal hydroxide such as NaOH, and an alcoholic solvent such as methanol. The reaction results in a mixture of different regioisomers, i.e. 2,5-regioisomers, 2,4-regioisomers, and 3,4-regioisomers.

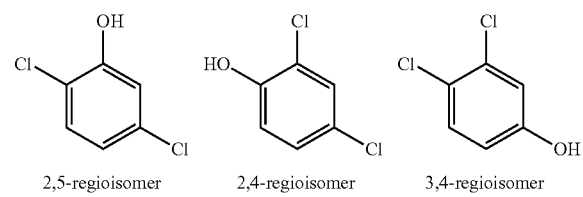 [SMILES: Oc1cc(Cl)ccc1Cl ; Oc1ccc(Cl)cc1Cl ; Oc1ccc(Cl)c(Cl)c1]

2,5-regioisomer    2,4-regioisomer    3,4-regioisomer

For example, hydrolyzing 1,2,4-trichlorobenzene in methanol using NaOH results in a mixture of 2,5-dichlorophenol, 2,4-dichlorophenol, and 3,4-dichlorophenol, and minor amounts of 2,5-dichlorophenol methyl ether, 2,4-dichlorophenol methyl ether, and 3,4-dichlorophenol methyl ether. The mixture typically comprises 40 to 95 wt.-%, preferably 50 to 85 wt.-%, more preferably 40 to 80 wt.-% of 2,5-dichlorophenol; 5 to 60 wt.-%, preferably 10 to 40 wt.-%, more preferably 10 to 20 wt.-% of 2,4-dichlorophenol; and optionally 0 to 30 wt.-%, preferably 5 to 25 wt.-%, more preferably 10 to 20 wt.-% of 3,4-dichlorophenol.

According to the present invention, a mixture (M) comprising 2,5-dichlorophenol, 2,4-dichlorophenol and optionally 3,4-dichlorophenol is subjected to a distillation step (i) to obtain a distillate (D). For example, a mixture obtained as described above obtained from hydrolyzation of 1,2,4-trichlorobenzene may be employed here. Alternatively, a mixture (M) may be obtained by combining a composition obtained from the mother liquor (L) in crystallization step (ii) with a fresh feed (F) comprising 2,5-dichlorophenol, 2,4-dichlorophenol and optionally 3,4-dichlorophenol. In this embodiment, a mixture obtained from hydrolyzing 1,2,4-trichlorophenol as described above may be employed as the feed (F).

Distillation typically removes most of the 3,4-dichlorophenol and increases the content of 2,5-dichlorophenol. Thus, in a preferred embodiment, distillate (D) comprises 2,5-dichlorophenol in an amount of 60 to 95 wt.-%, the reminder being mostly 2,4-dichlorophenol. For example, distillate (D) may comprise 50 to 95 wt.-%, more preferably 55 to 85 wt.-%, particular preferably 60 to 80 wt.-% of 2,5-dichlorophenol; and 5 to 50 wt.-%, more preferably 15 to 45 wt.-%, most preferably 20 to 40 wt.-% of 2,4-dichlorophenol.

Furthermore, distillation is carried out in a standard distillation column known in the art. Such standard columns may have a height of about 70 to 90 m, although according to the invention columns of lower height such as 25 to 60 m may be employed.

The distillation step (i) is carried out at reduced pressure, typically a pressure of about 5 kPa to 25 kPa, more preferably 5 kPa to 20 kPa, particular preferably 8 kPa to 20 kPa, and a bottom temperature of 60° C. to 230° C., more preferably 65° C. to 215° C., particular preferably 70° C. to 200° C. A person skilled in the art is aware that higher pressures require the use of higher temperatures. Separation of 2,5-dichlorophenol from 2,4-dichlorophenol during distillation is better at lower pressures. Thus, in one embodiment, the distillation step is carried out at a pressure of about 5 kPa to about 8 kPa and a column bottom temperature of 150° C. to about 156° C. On the other hand, the throughput may be reduced if the pressure is low. Therefore, in an alternative embodiment, the distillation step is carried out at a pressure of about 12 kPa to about 15 kPa and a column bottom temperature of 166° C. to about 176° C. If a balance increase in purity and throughput is desired during distillation, the distillation step may be carried out at a pressure of 8 kPa to about 12 kPa and a column bottom temperature of 156° C. to about 166° C. The column head temperature is in each case dependent on the boiling point of the given composition at the given pressure, and will typically be around 60° C.

According to the present invention, distillate (D) as obtained above is further subjected to a crystallization step (ii). In crystallization step (ii), a crystalline fraction (C) and a mother liquor (L) is obtained. The term "mother liquor" in this respect refers to the liquid residue resulting after removing the obtained crystals, irrespective of whether the liquid residue is a melt or a solution.

The crystalline fraction (C) obtained in the crystallization step (ii) comprises 2,5-dichlorophenol in a high degree of purity. The final purity as well as the separation efficiency obtained after crystallization can depend on various factors such as the duration of the crystallization or the degree of cooling during crystallization. The crystalline fraction (C) obtained in accordance with the present invention comprises 2,5-dichlorophenol in a degree of purity sufficient for use in chemical synthesis. However, if desired, even higher degrees of purity may be achieved. In a preferred embodiment, the crystalline fraction (C) obtained in step (ii) comprises 80 to 99.9 wt.-%, more preferably 85 to 99.9 wt.-%, particular preferably 90 to 99.9 wt.-% of 2,5-dichlorophenol, the remainder being mostly 2,4-dichlorophenol. A degree of purity suitable for chemical synthesis obtainable according to the invention is e.g. 80 to 99.9 wt.-%, preferably 85 to 97 wt.-% of 2,5-dichlorophenol in the crystalline fraction (C).

The crystallization step (ii) is performed in a crystallizer. Specific options as how to carry out the crystallization step are not particularly limited. Rather, any method of purifying 2,5-dichlorphenol using crystallization may be employed, e.g. recrystallization from water as described in DE 35 12 877. If crystallization from solution in a suitable solvent is used, it is necessary to remove the solvent from the obtained mother liquor (L) after crystallization before the composition obtained from the mother liquor (L) can be employed as described in preferred embodiments of the invention. Thus, in one embodiment, the crystallization step (ii) is carried out using crystallization from a melt. Further advantages of melt crystallization include smaller mass flows so that smaller units can be used. Melt crystallization in principle is known in the art. When melt crystallization is used, a liquid melt of distillate (D) is provided at high enough a temperature (typically between 20 and 55° C. and the liquid melt is allowed to cool slowly so that crystallization of 2,5-dichlorophenol can occur. Thus, the temperature during melt crystallization is typically lower than 55° C.

Crystallization from a melt can be carried out in various ways. In one embodiment layer melt crystallization is used. Layer melt crystallization can be carried out as known in the art, e.g. as described in U.S. Pat. No. 3,621,664, or in chapter 17.1.1. of Beckmann, W. (Ed.) (2013) Crystallization. Basic Concepts and Industrial Applications. Wiley-VCH Verlag, Weinheim, Germany. Layer melt crystallization can be done e.g. as static layer melt crystallization or dynamic layer melt crystallization. In one embodiment, layer melt crystallization is carried out as static layer melt crystallization.

In a preferred embodiment, suspension melt crystallization may be used. For suspension melt crystallization, a vessel with stirrer and internal or external heat exchange for batch or continuous mode, followed by a separation unit is typically employed. For example, suspension melt crystallization may be carried out using agitated vessels with internal or external cooling, such as a cooling disk crystallizer, or a scraped surface crystallizer. Suspension layer melt crystallization typically also includes a solid/liquid separation step. Suitable equipment for solid/liquid separation can be operated batchwise or continuously and includes e.g. filters, such as drum or belt filters, filter presses or a pressure nutsch, centrifuges, such as a pusher centrifuge or worm screw screw centrifuge, or wash columns.

In a preferred embodiment of the present invention, the composition obtained from the mother liquor (L) is recycled into the distillation step. Although crystallization as described above is suitable to finally obtain a high degree of purity, it has to be noted that large amounts of the desired 2,5-dichlorophenol naturally remain in the mother liquor (L). For example, the composition obtained from the mother liquor (L) may comprise 2,5-dichlorophenol in an amount of 30 to 90 wt.-%, more preferably 35 to 90 wt.-%, particular preferably 40 to 90 wt.-% of 2,5-dichlorophenol, the remainder being mostly 2,4-dichlorophenol. Therefore, by recycling the composition obtained from the mother liquor (L) into the distillation step, the overall purification efficiency or yield, i.e. the total amount of pure 2,5-dichlorophenol obtained from a given crude composition, can be increased.

In one embodiment, recycling the composition obtained from the mother liquor (L) into the distillation step is carried out by combining a composition obtained from the mother liquor (L) in step (ii) with a feed (F), comprising 2,5-dichlorophenol, 2,4-dichlorophenol and optionally 3,4-dichlorophenol, to obtain mixture (M) to be subjected to distillation in step (i). As mentioned above, a mixture obtained from hydrolyzing 1,2,4-trichlorophenol as described herein may be employed here. This step can be performed in a suitable mixer as known in the art. Suitable mixers are not specifically limited and could e.g. a simple vessel with a stirrer. The mixing ratio of feed (F) to the composition obtained from the mother liquor (L) can be adjusted as desired, depending e.g. on the desired overall purification efficiency, the desired final purity or the desired throughput. If higher amounts of fresh feed (F) over the composition obtained from the mother liquor (L) are used, the throughput can be increased but the overall purification efficiency and/or purity may suffer.

The above process is not limited to the use of only one distillation column or only one crystallizer. Rather, configurations involving more than one distillation column and/or more than one crystallizer are possible. For example, the initial composition may be fed to a first distillation column, the resulting first distillate is fed to a second distillation column, the resulting second distillate is subjected to crystallization, and the composition obtained from the mother liquor is recycled into the second distillation column optionally after being combined with some portion of first distillate. Furthermore, the crystalline fraction obtained in a first crystallizer may again be subjected to crystallization and the mother liquor obtained in the second crystallization step can be recycled into the first crystallization step optionally after combination with a distillate obtained in accordance with the present invention.

The purification process according to the present invention can be carried out on an industrial scale, e.g. in a continuous or batchwise manner. The process according to the invention provides 2,5-dichlorophenol in a high degree of purity with a high overall purification efficiency.

The invention claimed is:

1. A process for purifying 2,5-dichlorophenol, the process comprising the steps of:
   (i) subjecting a mixture (M) comprising 2,5-dichlorophenol, 2,4-dichlorophenol and optionally 3,4-dichlorophenol to distillation to obtain a distillate (D), and
   (ii) subjecting the distillate (D) to a melt crystallization step to obtain a crystalline fraction (C) and a mother liquor (L).

2. The process of claim 1, further comprising the step of:
   (iii) combining a composition obtained from the mother liquor (L) in step (ii) with a feed (F), comprising 2,5-dichlorophenol, 2,4-dichlorophenol and optionally 3,4-dichlorophenol, to obtain mixture (M) to be subjected to distillation in step (i).

3. The process of claim 2, wherein the feed (F) is obtained from hydrolyzing 1,2,4-trichlorophenol in the presence of an alkali metal hydroxide or alkali metal alkoxide.

4. The process of claim 2, wherein the mixture (M) and/or the feed (F) comprises 40 to 95 wt.-% of 2,5-dichlorophenol; 5 to 60 wt.-% of 2,4-dichlorophenol; and optionally 0 to 30 wt.-% of 3,4-dichlorophenol.

5. The process of claim 1, wherein the distillate (D) obtained in step (i) comprises 50 to 95 wt.-% of 2,5-dichlorophenol.

6. The process of claim 1, wherein the crystalline fraction (C) obtained in step (ii) comprises 80 to 99.9 wt.-% of 2,5-dichlorophenol.

7. The process of claim 1, wherein the distillation step (i) is carried out in a distillation column at a pressure of 5 kPa to 25 kPa, and a bottom temperature of 60° C. to 230° C.

8. The process of claim 1, wherein the melt crystallization step (ii) is carried out using layer melt crystallization or suspension melt crystallization.

9. The process of claim 8, wherein the step of suspension melt crystallization further comprises a step of separating the obtained crystals from the melt.

10. The process of claim 2, wherein 2,5-dichlorophenol is present in the mixture (M) and/or the feed (F) in an amount of 50 to 85 wt.-%.

11. The process of claim 10, wherein 2,5-dichlorophenol is present in the mixture (M) and/or the feed (F) in an amount of 40 to 80 wt-%.

12. The process of claim 11, wherein 2,4-dichlorophenol is present in the mixture (M) and/or the feed (F) in an amount of 10 to 40 wt-%.

13. The process of claim 12, wherein 2,4-dichlorophenol is present in the mixture (M) and/or the feed (F) in an amount of 10 to 20 wt.-%.

* * * * *